United States Patent
Wang et al.

[11] Patent Number: 5,876,341
[45] Date of Patent: Mar. 2, 1999

[54] REMOVING BEAM INTERLEAVE EFFECT ON DOPPLER SPECTRUM IN ULTRASOUND IMAGING

[75] Inventors: Hong Wang, Bellevue; John Klepper, Seattle; Lin-Xin Yao, Bellevue; Tai-Kyong Song; Zuhua Mao, both of Issaquah, all of Wash.

[73] Assignee: Siemens Medical Systems, Inc., Iselin, N.J.

[21] Appl. No.: 885,075

[22] Filed: Jun. 30, 1997

[51] Int. Cl.⁶ .................................................... A61B 8/06
[52] U.S. Cl. ........................................... 600/441; 600/455
[58] Field of Search .................................. 600/441, 443, 600/454–455

[56] References Cited

U.S. PATENT DOCUMENTS

| | | |
|---|---|---|
| Re. 35,371 | 11/1996 | Seo . |
| 4,398,540 | 8/1983 | Takemura et al. . |
| 4,632,124 | 12/1986 | Hiller et al. . |
| 5,152,292 | 10/1992 | Karp . |
| 5,301,670 | 4/1994 | Sato et al. . |
| 5,363,851 | 11/1994 | Hall et al. . |
| 5,441,052 | 8/1995 | Miyajima . |
| 5,501,223 | 3/1996 | Washburn et al. . |
| 5,544,658 | 8/1996 | Kim et al. . |
| 5,662,115 | 9/1997 | Torp et al. ............................ 600/455 |

*Primary Examiner*—Francis J. Jaworski

[57] ABSTRACT

A BcD mode ultrasound imaging system including a Doppler processor which is configured to receive a Doppler signal having components that are corrupted by residue from color mode interleaving. The Doppler processor is configured to analyze the residue effect and compensate for the residue by filtering the received Doppler signal.

22 Claims, 6 Drawing Sheets

FIG. 1

REMOVING BEAM INTERLEAVE EFFECT ON DOPPLER SPECTRUM IN ULTRASOUND IMAGING

BACKGROUND OF THE INVENTION

1. Field of the Invention

The present invention relates to ultrasound imaging and, more particularly, to a color Doppler ultrasound imaging system.

2. Description of the Related Art

Ultrasound imaging devices are known which support simultaneous B mode, color mode, and Doppler mode imaging (referred to as "BcD mode" imaging). In such systems, the B mode ultrasound produces a two-dimensional tomographic image of the object being scanned, and the color and Doppler modes are used to generate an image of blood flow or tissue fluid movement information that is spatially coordinated with and superimposed upon the B mode two-dimensional tomographic image.

Doppler ultrasound is based on the Doppler effect, which is a change in frequency caused by the relative motion of a wave source, a receiver and a reflector. As applied to medical applications, an ultrasound transducer embodying the source and receiver is stationary while blood or tissue fluid is the moving reflector. The change in frequency detected is the difference between the transmitted ultrasound signal frequency and the reflected ultrasound signal frequency. The change is a function of the transmitted signal frequency, the propagation speed of the transmitted signal through the patient's anatomy, the speed of flow in the range gate and the angle of incidence between the ultrasound signal and the direction of blood flow.

In B mode imaging, ultrasonic pulses are radiated to a subject and the radiation direction is scanned in order to obtain the tomographic image. In Doppler mode, ultrasonic pulses are transmitted repeatedly in respective directions in which ultrasonic waves are radiated, and a Doppler shift frequency is detected based on the phase variation of the reflected waves. More particularly, to obtain the blood flow data, an ultrasound probe or transducer is driven to repeatedly radiate ultrasonic waves in a particular direction for a number of times, and the received signal is detected by an orthogonal phase detecting circuit, thereby obtaining a Doppler shift signal on the basis of blood or fluid flow.

The Doppler shift signal is frequency analyzed by a frequency analyzing circuit to find an average value of the Doppler shift, an average power of the Doppler shift, etc. A blood flow velocity color flow mapping image is obtained by a Fast Fourier Transform (FFT) circuit and the blood flow velocity color flow mapping image and a B mode image are provided to a digital scan converter. The images are then read out of the scan converter and the two-dimensional blood flow velocity color flow mapping image is superimposed on the B mode display on a monitor.

In BcD mode imaging, color mode transmission vectors are typically interleaved with Doppler vectors or pulses, rather than transmitted successively. The interleaving is defined by an interleave factor, which refers to the number of color vectors sent between the Doppler vectors. Interleaving color mode vectors with the Doppler vectors is necessary in order to increase frame rate (i.e., the rate of image display). However, interleaving the color mode vectors with the Doppler vectors can result in a residue effect, which result from reflections of the interleaved waves that have not yet died out before the Doppler reading occurs. If there is any residue signal due to the color, the Doppler signal will be corrupted. This can result in inaccurate data and what is referred to as broken tone artifacts.

Accordingly, there is a need for a BcD mode ultrasound system in which broken tone artifacts due to the interleaving factor of the color mode on the Doppler spectrum is eliminated. There is a still further need for a Doppler ultrasound system in which Doppler signals are optimized.

SUMMARY OF THE INVENTION

These and other drawbacks of the prior art are overcome in large part by a BcD mode ultrasound imaging system according to the present invention. A BcD mode ultrasound imaging system according to the present invention includes a Doppler processor which is configured to receive a Doppler signal having components that are corrupted by residue from color mode interleaving. The Doppler processor analyzes the residue effect and corrects for the residue by performing a compensation function on the received Doppler signal.

The beam interleave effect on Doppler ultrasound has been found to result in a weighting on each Doppler frequency component based on the interleave factor. According to the present invention, the interleave factor is used to calculate a weighting correction and correct the Doppler signal.

BRIEF DESCRIPTION OF THE DRAWINGS

A better understanding of the present invention is obtained when the following detailed description is considered in conjunction with the following drawings in which:

FIG. 1 is a diagram illustrating color and Doppler interleaving;

DETAILED DESCRIPTION OF THE INVENTION

Figure 1:
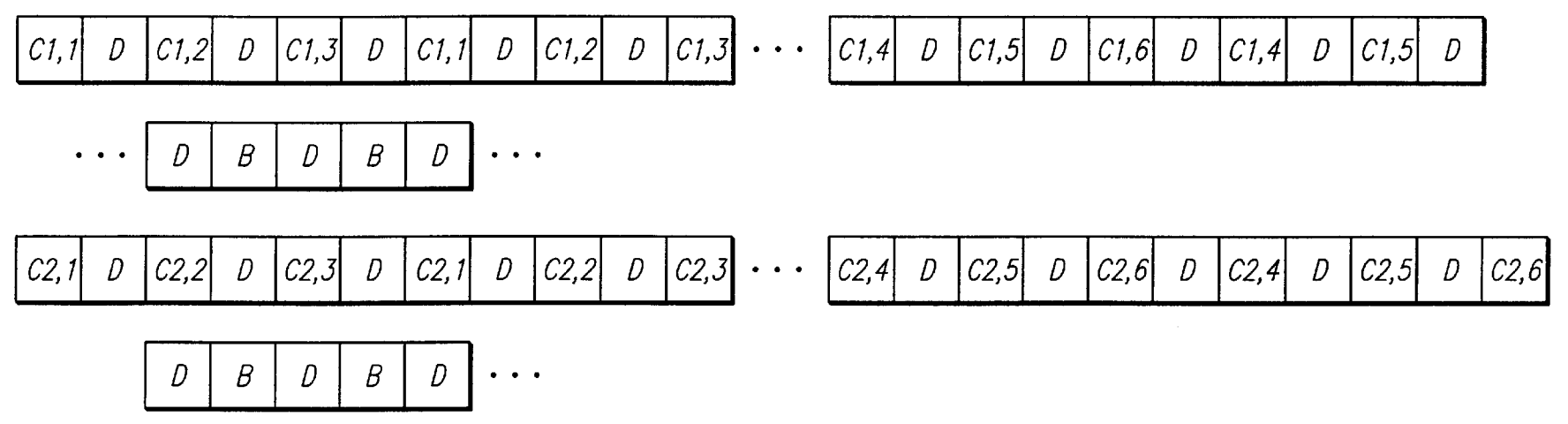

Turning now to the drawings, and with particular attention to FIG. 1, a diagram showing interleaving of Doppler, and color mode firings is illustrated. The Doppler vectors are represented by the letter D; the color vectors are represented by the letter C, and B mode vectors by the letter B. According to one embodiment, each color frame requires sixty lines, for which each line is sampled 12 times. Rather than sequentially sampling each color line 12 times, however, a circular sampling based on the interleave factor occurs. Thus, if the interleave factor is 3, three color lines will be sampled in order, then they will be sampled again, and so on until each has been sampled 12 times. Once each set of three lines has been sampled twelve times, the process repeats for the next three lines. One color line is sampled between every Doppler vector. The color lines are sampled based on their interleave frequency. Thus, in FIG. 1, $C_{1,1}$, $C_{1,2}$, $C_{1,3}$, $C_{1,4}$, $C_{1,5}$, and $C_{1,6}$ represent sampling of the color lines 1, 2, 3, 4, 5 and 6 of frame 1; $C_{2,1}$, $C_{2,2}$, $C_{2,3}$, $C_{2,4}$, $C_{2,5}$, $C_{2,6}$ represent sampling of lines 1, 2, 3, 4, 5 and 6; of frame 2 and so on. Between the sampling of the color lines the B mode vectors are sampled. It is noted that while the present invention is described with respect to this particular sequence of interleaving, others are possible. Thus, FIG. 1 is exemplary only.

Figure 5A:
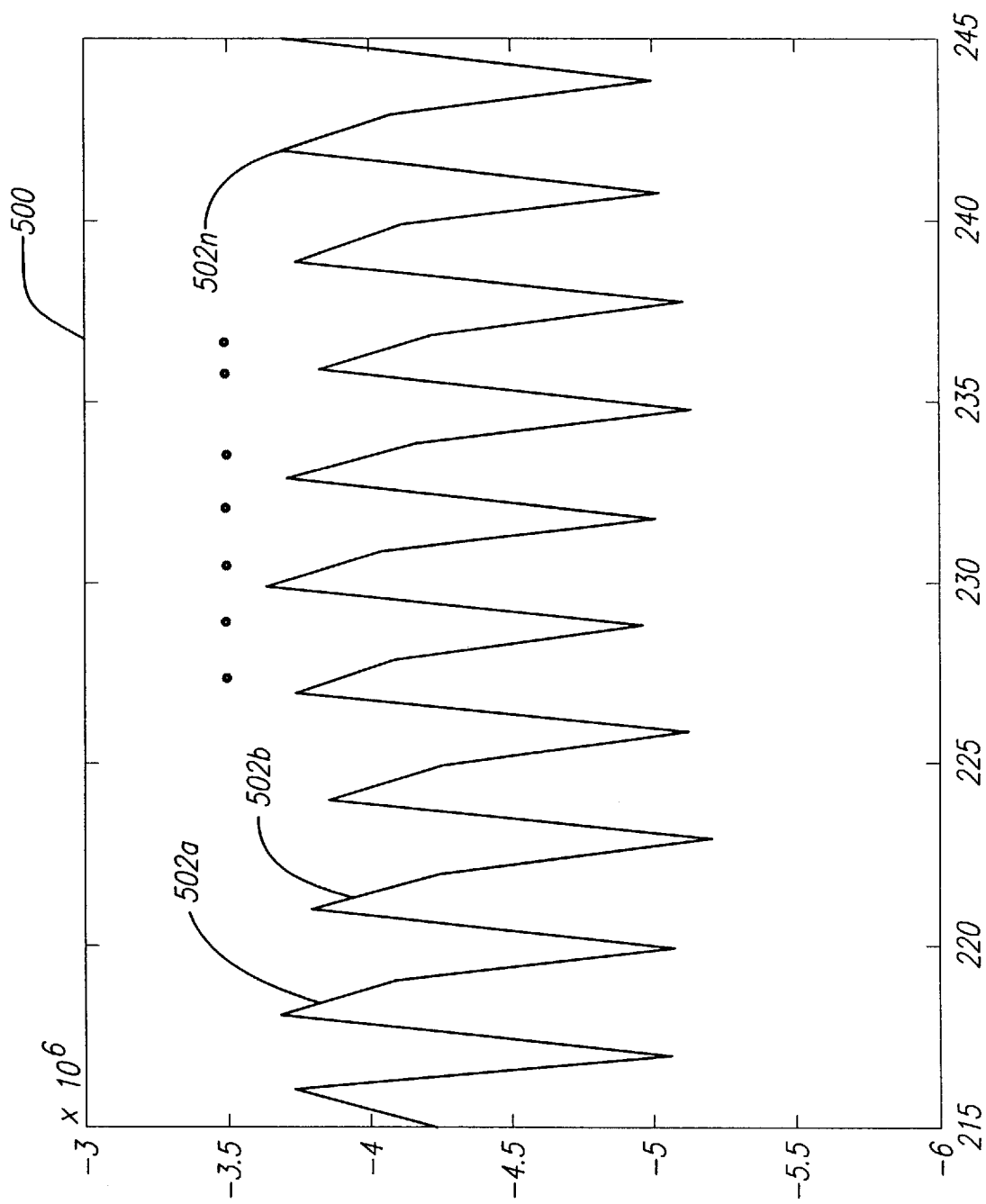
FIG. 5a is a diagram showing the effect of color interleaving on Doppler spectrum.
Figure 5B:
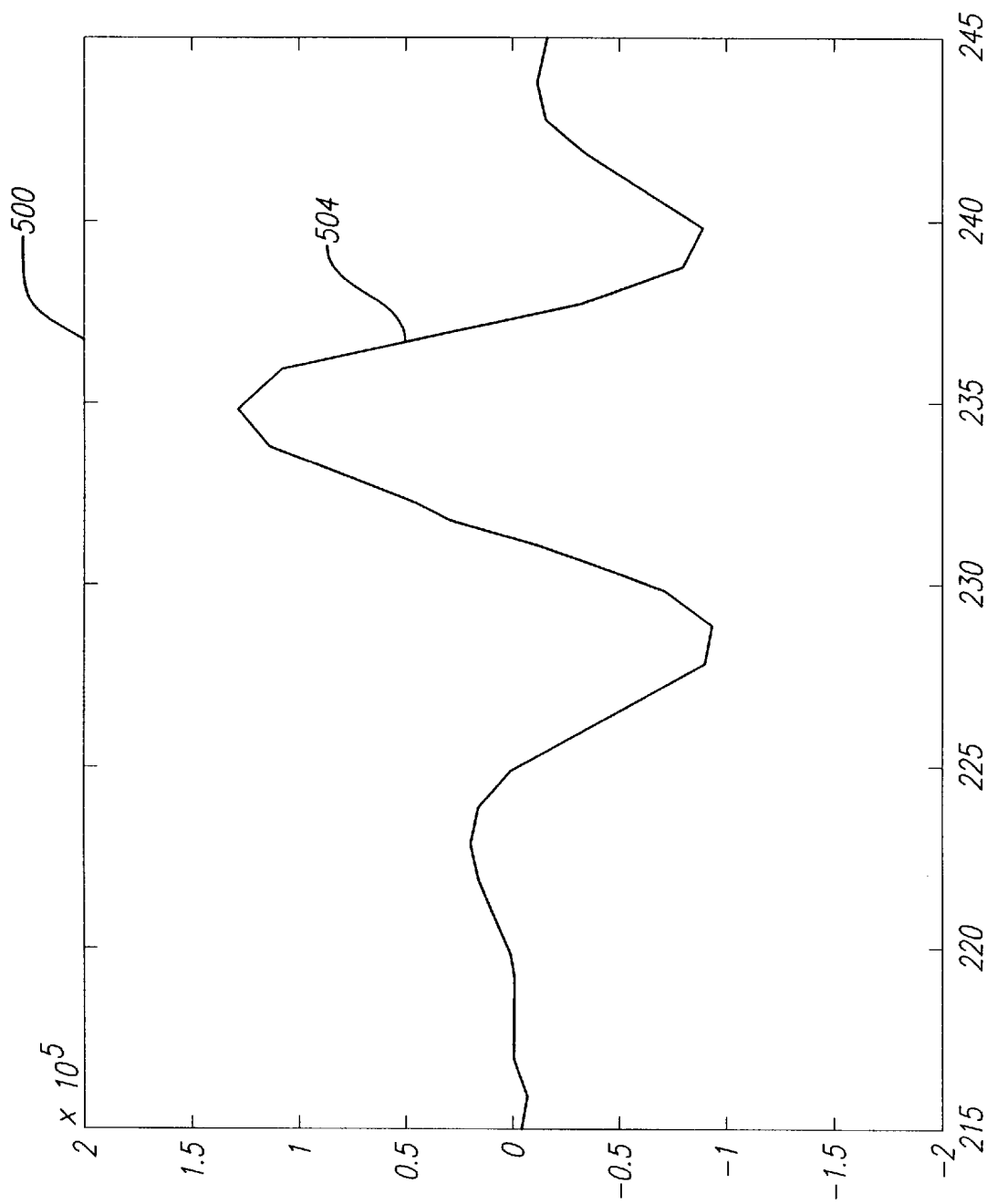
FIG. 5b is a diagram illustrating a Doppler spectrum that has been corrected for color interleaving.

A exemplary Doppler spectrum showing the effect of color mode interleaving is shown in FIG. 5*a*. The spectrum shows a Doppler wave 500*a*, corrupted with broken tone artifacts due to the color mode interleaving. The broken tone artifacts are visible as the spikes 502*a*–4502*n*. A system according to the present invention compensates for the interleave effect. More particularly, a Doppler spectrum 500*b* that has been filtered according to the present invention is shown in FIG. 5*b*. As can be seen, the broken tone artifacts (i.e., the spikes 502*a*–502*n*) are virtually eliminated, leaving a relatively clean Doppler pulse.

The method according to the present invention will now be derived. A received (time domain) Doppler signal during C and D firing in BcD mode can be described by Equation 1:

$$S_n = A\cos(\omega_b nT + \phi) + B\cos(\omega_w nT + \phi) + C_m + D + e_n \quad (1)$$

where $S_n$ is the nth sampled Doppler signal, while $\omega_b$ and $\omega_w$ are Doppler frequencies of blood flow and blood vessel wall, A and B are the amplitudes of the blood and wall signals, T is the pulse repetition period, $\phi$ and $\theta$ are the phases of blood and wall signals, $C_m$ is the residue signal from firing the Mth color lines, D is the reflected signal from stationary scatterers and $e_n$ is the signal noise. It is noted that Equation 1 is exemplary only in that only one (each) blood flow and vessel frequency component is shown.

In BcD mode, if the interleave factor for color form mapping is M (i.e., the system circularly fires M color lines between Doppler firings) the received series of Doppler signals $\tilde{S}_n$ is given by Equation 2:

$$\tilde{S}_n = S_n - S_{(n-M)} \quad (2)$$

From Equation 2, using the standard trigonometric relations, Equation 3 can be derived:

$$\tilde{S}_n = 2A\sin\frac{\omega_d MT}{2}\sin\left(\frac{\omega_d(2n+MT)}{2}+\phi\right)+ \\ 2B\sin\frac{\omega_w MT}{2}\sin\left(\frac{\omega_w(2n+MT)}{2}+\theta\right)+e_n-e_{(n-M)} = \\ 2A\sin\frac{\omega_d MT}{2}\sin(\omega_d nT+\tilde{\phi})+2B\sin\frac{\omega_w MT}{2}\sin(\omega_w nT+\tilde{\theta})+\tilde{e}_n \quad (3)$$

where $\tilde{\phi}=\omega_d MT/2+\phi$, $\tilde{\theta}=\omega_w MT/2+\theta$ and $\tilde{e}_n=e_n-e_{(n-M)}$.

The received Doppler signal series $\tilde{S}_n$ thus can be seen to have a weighting factor F of $\sin(\omega MT/2)$ for each frequency $\omega$. In order to restore the spectrum of $S_n$ from $\tilde{S}_n$, the weighting factor F for each frequency must be removed. As will be discussed in greater detail below, a Doppler processor according to the present invention performs the weighting correction function. More particularly, in the frequency domain, after a Fourier transform operation, each frequency component is weighted by F. A correction according to the present invention applies a (1/F) factor to each frequency component to compensate for the weighting factor F on the Doppler spectrum.

It is noted that, in the frequency domain at certain frequencies, the weighting factor $\sin(\omega MT/2)$ can have singular values or zeros when $\omega MT/2 = L\pi$, where L=0, ±1, ±2, . . . To avoid this problem at those frequencies which cause the zero values, the weighting factor $\sin(\omega MT/2)$, can be redefined as in Equation 4:

$$F = \begin{cases} \sin\frac{\omega MT}{2}, & \text{if}\left|\sin\frac{\omega MT}{2}\right| \geq \sigma \\ sgn\left(\sin\frac{\omega MT}{2}\right)\sigma, & \text{if}\left|\sin\frac{\omega MT}{2}\right| < \sigma \end{cases} \quad (4)$$

where $0 \leq \sigma \leq 1$. The threshold value $\sigma$ is determined according to spectrum noise level, or chosen empirically. More particularly, the threshold $\sigma$ is greater the higher the noise level and generally optimized. Thus, in the frequency domain, a function of (1/F) is applied for each frequency $\omega$.

In order to further optimize the Doppler spectrum, additional processing related to successive sets of color lines may be performed. More particularly, after M color lines have been finished, (i.e., after each set of M color lines), another M color lines are scanned. For example, the set of color lines beginning with $C_{1,4}$ in FIG. 1 are scanned after the scanning of the first three color lines. At this transition (i.e., as $C_{1,4}$ begins), the residue signals of color mode vectors on the Doppler spectrum will be different due to unwanted spikes from start-up. Accordingly, in one embodiment, the M Doppler transition samples are forced to zero. Thus, for example, the D pulse in FIG. 1 immediately following $C_{1,4}$ may be forced to zero. Window functions, such as Hanning or Hamming windows or other window functions, are applied to the other samples in order to minimize artifacts that may be introduced by color line transitions. A Hamming filter thus has the following form (in the time domain):

$$W = 5\left(1+\cos\frac{2\pi k}{L-1}\right) \quad (5)$$

Here, window length is chosen according to the formula M·S, where M is the interleave factor, and S is the sample size. In the example above, a window size of 36 is used (3×12).

Figure 2:
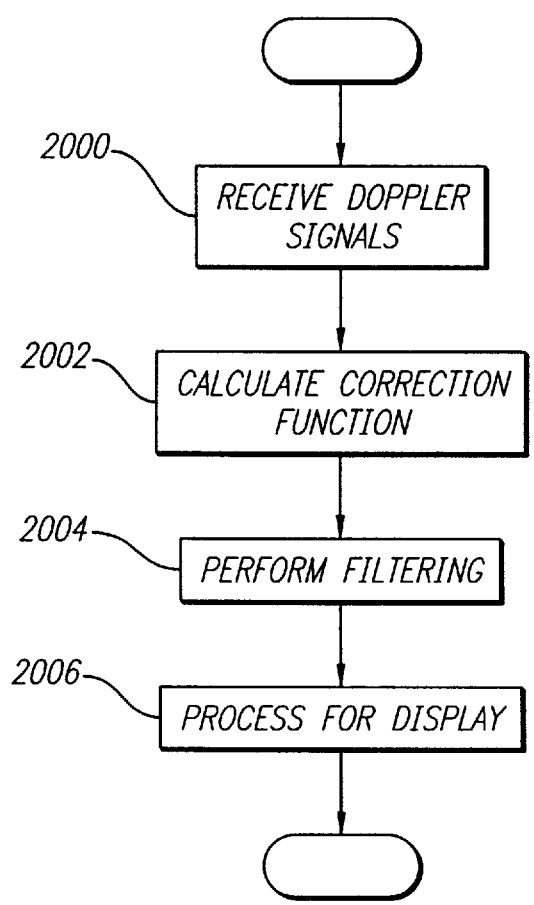
FIG. 2 is a flowchart illustrating a method according to one embodiment of the present invention.

Turning now to FIG. 2, a flow chart illustrating a method according to one embodiment of the invention is shown. More particularly, in an initial step 2000, Doppler signals are received. The Doppler signals may be corrupted with color interleave signals. In a step 2002, after the input Doppler signal is Fourier transformed, a weighting factor F, for the weighting of each frequency component due to the filtering, is determined. In one embodiment, the weighting factor is as set forth in Equation 4, above. The correction factor (1/F) is then applied to each frequency component of the Fourier transformed Doppler signal. This occurs in a step 2004. Finally, the corrected Doppler signal is processed for display in a step 2006.

Figure 3:
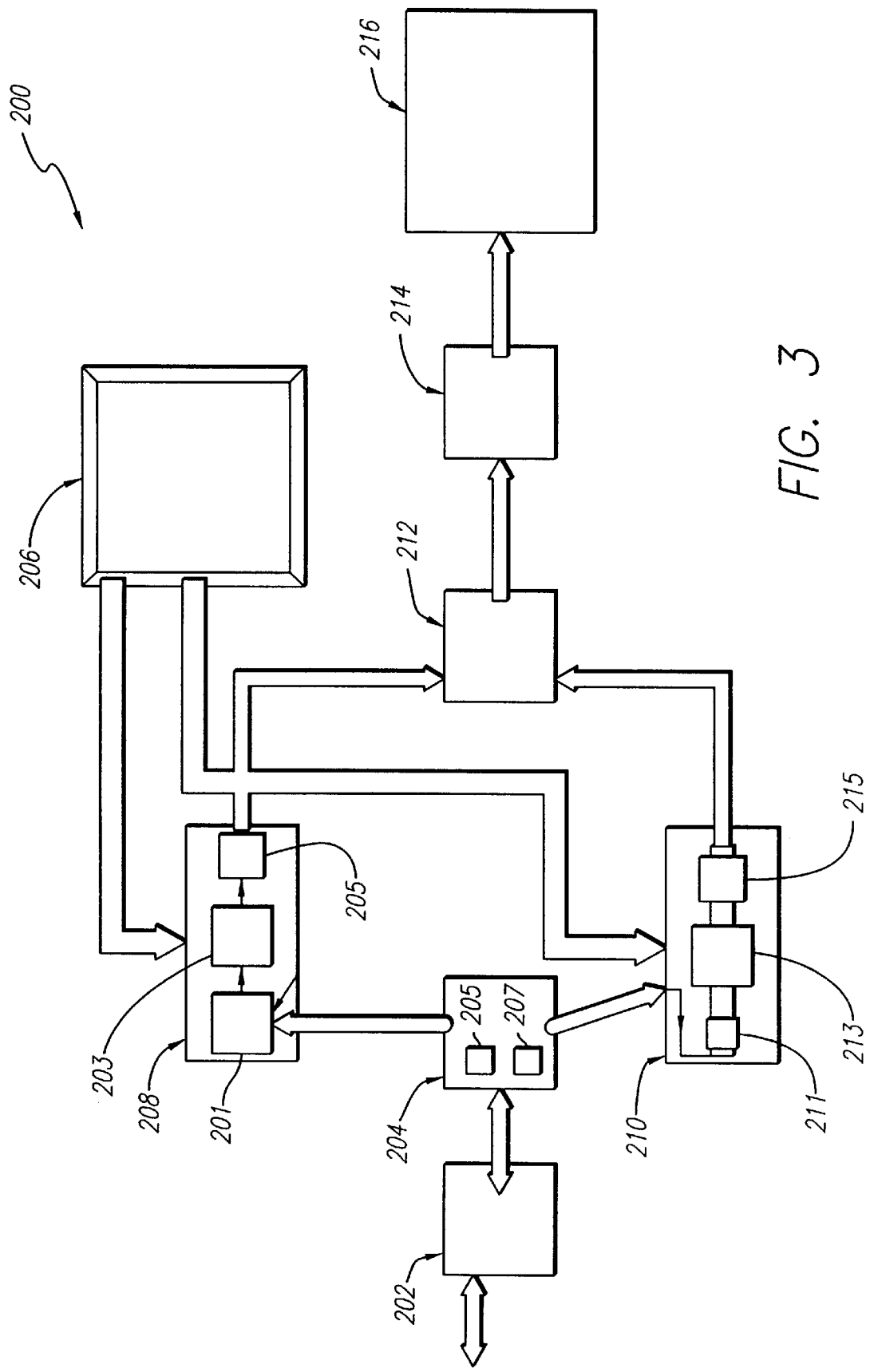
FIG. 3 is a block diagram of an ultrasound imaging system according to an embodiment of the present invention.

Turning now to FIG. 3, a block diagram of an ultrasound imaging system according to an embodiment of the present invention is illustrated. The ultrasound imaging system 200 includes a transducer probe 202 configured to radiate and receive ultrasound waves. The transducer probe 202 is coupled to a transmit/receive circuit 204, a B mode processor 208 and a Doppler processor 210. The B mode processor 208 and Doppler processor 210 are, in turn, coupled to a scan converter 212, which provides an output to a color processor 214 and finally to a display device 216. A controller 206 is further coupled to control the various devices. It is noted that, while the various functions are illustrated as being implemented as discrete hardware components, they may be implemented in varying degrees of integration as ASICs (application specific integrated circuits) or microprocessors, or software. Thus, FIG. 3 is exemplary only.

The exemplary transmit/receive circuit 204 includes a gated oscillator 205 and a gated receiver 207. The system controller 206 provides a user interface (e.g., control panel, display menu, keyboard and the like) (not shown) and generally controls system operations. In operation, the system controller 206 triggers the gated oscillator 205 to generate electrical signals for output to the transducer probe 202. The transducer probe 202 converts the electrical signals into a Doppler ultrasound transmit pulse wave pattern. Typically, the transducer is positioned adjacent to and in contact with a patient's anatomy. The transmit pulse wave pattern propagates into the patient's anatomy where it is refracted, absorbed, dispersed and reflected. The signal components which are reflected back to the transducer probe 202 are sensed and converted back into electrical signals. The signals are then input to the receiver 207, which amplifies the signals.

The B mode signals are transferred to the B mode processor 208. The B mode processor 208 includes, for example, a logarithmic amplifier 201, an envelope detector 203, and an A/D converter 205. The logarithmic amplifier logarithmically amplifies the signal from the scan converter 204. The envelope detector 203 then detects the envelope of the signal, which is then digitized in A/D converter 205. The output from the B mode processor 208 is then provided to a scan converter 212. The scan converter 212 is provided because the received signals are in a vector domain (or polar coordinates), whereas the display device is in raster domain (or rectangular coordinates). The scan converter 212 thus converts the received polar coordinate image into raster coordinate display and interpolates outputs for those raster pixel locations which do not exactly coincide with the received vector points. The scan converter 212 outputs the B mode image to a color processing circuit 214 which then provides the output to the display device 216.

With regard to the Doppler pulses, a pulse wave form is transmitted and echoes responsive to the pulse are detected. To define the pulse, the oscillator 205 is gated. To sense echo response to the pulse, the receiver 207 is also gated. Thus, time windows are defined for transmitting and receiving the ultrasound energy.

The converted echo signals are fed to the Doppler processor 210. The Doppler processor 210 is a special purpose signal processor or a general purpose processor programmed to perform Doppler processor functions. According to an embodiment of the present invention, the Doppler processor 210 receives a Doppler signal and detects the Doppler shift frequency by an orthogonal detection method. More particularly, as will be discussed in greater detail below, the Doppler processor 210 includes quadrature detectors 211, which include mixers (not shown) having reference frequency phases differing by 90 degrees and having frequencies the same as the transmission frequency. Alternatively, 90 degree phase shifting may be provided to the input signals, and the mixers may have no phase difference. Accordingly, the outputs from lowpass filters (not shown) in quadrature detectors 211 are the complex Doppler frequencies that have been shifted by the Doppler effects, as well as being complex signals having phases differing by 90 degrees (i.e., the received Doppler signals thus have in-phase and quadrature components). The equations for both the in-phase and quadrature components are set forth in Equation 2 above. The Doppler processor 210 further includes color interleave correction unit 213, which as described above, compensates for the weighting effect on the Doppler spectrum. Finally, the Doppler processor 210 includes velocity estimation circuitry 215, which in one embodiment performs Fast Fourier Transforms on the received signals and also computes other blood flow parameters such as variance and power.

More particularly, according to the present invention, the Doppler processor 210 includes circuitry to correct for the residue effect of interleaving the color mode vectors with the Doppler mode vectors. More particularly, since the received in-phase and quadrature components of the received Doppler signals will be processed according to Equation 2 above, a correction function according to Equation 4 is provided to compensate for the weighting effect of Equation 3. Additionally, a zeroforcing function and window function, for example according to Equation 5, may be provided to correct for line errors when transitions occur between sampling of color lines. As discussed above, the correction for the color mode interleaving is dependent upon the interleave factor. Thus, the system controller 206 provides control signals to the Doppler processor 210 which identify the interleave factor which is used by the Doppler processor to correct for the color mapping mode residue errors.

The corrected Doppler signal is then provided to the velocity estimation circuitry 215 which, as discussed above, provides an output to the scan converter 212 which, when necessary, alters the scanning direction of the input blood flow data and outputs the resultant data and performs frame interpolation.

Figure 4:
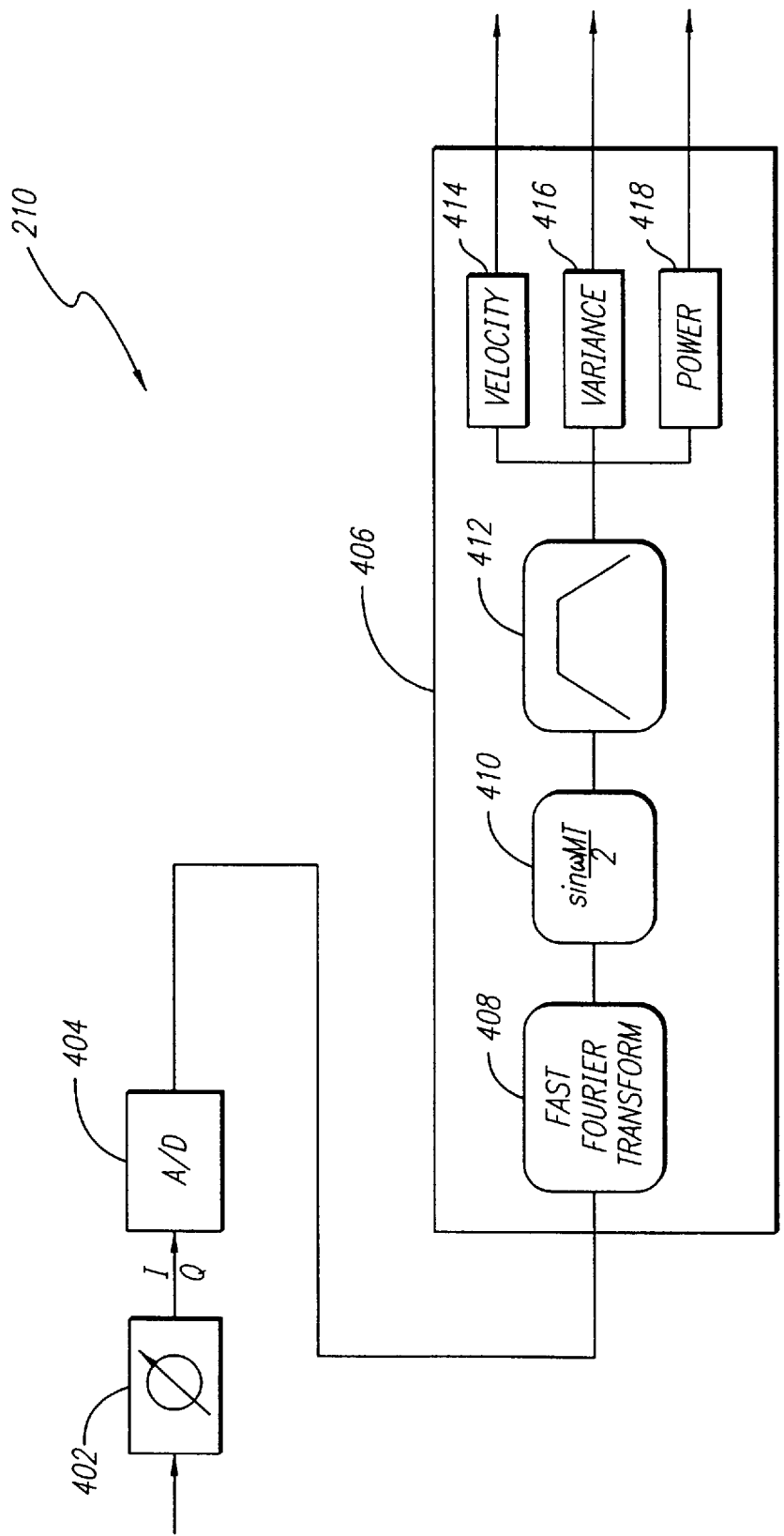
FIG. 4 is a block diagram illustrating a Doppler processor according to an embodiment of the present invention.

Turning now to FIG. 4, a diagram illustrating operation flow of a Doppler processor 210 according to one embodiment of the present invention is illustrated. More particularly, the Doppler processor 210 includes a filtering, mixing and/or phase shifting unit 304 to convert the received Doppler signals into their in-phase and quadrature components. The unit 304 thus may include one or more mixers and phase shifters, as well as low pass filters. The in-phase and quadrature components may then be high pass filtered to remove the effect of blood vessel walls on the blood flow signal. The filtered in-phase and quadrature components are then provided to an analog-to-digital converter 404 where they are digitized. The digitized in-phase and quadrature signals are then provided to filter correction circuitry 406. The weighting unit 406 includes a Fast Fourier Transform stage 408 to perform a Fast Fourier Transform on the received time domain signals. The frequency domain signals are then provided to the color mode interleave correction unit 410 and window filter 412. The color mode correction unit 410 thus implements a correction of the weighting function of Equation 4 on each frequency. The window function filter 412 is provided to correct for errors resulting from color mode transitions. Finally, the filtered signals are provided to a velocity circuit 414, a variance circuit 416, and a power circuit 41 8 before being provided to the scan converter. It is noted that the system illustrated in FIG. 4 is exemplary only; for example, digital-to-analog conversion may occur before the received signals are processed by the circuitry 304. Moreover, as discussed above, the Doppler processor 210 may be embodied as an ASIC or a microprocessor.

The invention described in the above detailed description is not intended to be limited to the specific form set forth herein but, on the contrary, it is intended to cover such alternatives, modifications and equivalents as can reasonably be included within the spirit and scope of the appended claims.

What is claimed is:

1. A system configured for color mode and Doppler display, comprising:
   means for generating and interleaving a plurality of transmit color pulses with a plurality of transmit Doppler pulses;
   means for receiving a plurality of receive Doppler signals and a plurality of receive color mode signals, said signals representative of receive color pulses and receive Doppler pulses corresponding to said transmit color pulses and said transmit Doppler pulses; and
   means for compensating for a residue effect of said color mode signals on said Doppler signals as a result of said color mode interleaving.

2. An ultrasound imaging system according to claim 1, wherein said compensating means includes means for forcing predetermined transition Doppler signals to approximately zero.

3. An ultrasound imaging system according to claim 2, wherein said performing means includes means for performing one or more filter functions on one or more remaining samples.

4. A system according to claim 3, wherein said one or more filter functions includes one or more window functions.

5. An ultrasound imaging system, configured for color mode and Doppler display, comprising:
   means for interleaving a plurality of transmit color pulses with a plurality of transmit Doppler pulses;
   means for receiving Doppler signals and color mode signals said signals representative of receive color pulses and receive Doppler pulses corresponding to said transmit color pulses and said transmit Doppler pulses; and
   means for compensating for an effect of said color mode signals on said Doppler signals, said means for compensating including means for performing one or more filter functions, wherein said performing means includes means for executing a weighting correction function at a plurality of frequencies $\omega$ having the form (1/F), where F has the form:

$$F = \begin{cases} \sin\frac{\omega MT}{2}, & \text{if } |\sin\frac{\omega MT}{2}| \geq \sigma \\ sgn\left(\sin\frac{\omega MT}{2}\right)\sigma, & \text{if } |\sin\frac{\omega MT}{2}| < \sigma \end{cases}$$

6. A system, configured for color mode and Doppler display, comprising:
   means for interleaving a plurality of transmit color pulses with a plurality of transmit Doppler pulses;
   means for receiving Doppler signals and color mode signals, said signals representative of receive color pulses and receive Doppler pulses corresponding to said transmit color pulses and said transmit Doppler pulses; and
   means for compensating for an effect of said color mode signals on said Doppler signals, said compensating means including means for performing one or more filter functions, wherein said performing means compensates for a weighting of the form sin($\omega$MT/2), where $\omega$ is the frequency, and M is the interleave factor.

7. A method for ultrasound imaging in a system configured for color mode and Doppler display, the method comprising:
   interleaving a plurality of transmit color pulses with a plurality of transmit Doppler pulses;
   receiving Doppler signals and color mode signals representative of receive Doppler pulse signals and receive color mode signals, corresponding to said color pulses and said Doppler pulses; and
   compensating for a residue effect of said color mode signals on said Doppler signals as a result of said color mode interleaving.

8. A method for ultrasound imaging according to claim 7, wherein said compensating includes forcing predetermined transition Doppler signals to approximately zero and performing one or more filter functions.

9. A method for ultrasound imaging according to claim 8, wherein said performing includes filtering with a window function.

10. A method for ultrasound imaging in a system configured for color mode and Doppler display, the method comprising:
    interleaving a plurality of color pulses with a plurality of Doppler pulses;
    receiving Doppler signals and color mode signals representative of receive Doppler pulse signals and receive color mode signals, corresponding to said color pulses and said Doppler pulses; and
    compensating for an effect of said color mode signals on said Doppler signals including performing one or more filter functions; wherein said performing includes compensating using a weighting correction (1/F at each frequency $\omega$ where F has the form:

$$F = \begin{cases} \sin\frac{\omega MT}{2}, & \text{if } |\sin\frac{\omega MT}{2}| \geq \sigma \\ sgn\left(\sin\frac{\omega MT}{2}\right)\sigma, & \text{if } |\sin\frac{\omega MT}{2}| < \sigma \end{cases}$$

11. A method for ultrasound imaging in a system configured for color mode and Doppler display, the method comprising:
    interleaving a plurality of color pulses with a plurality of Doppler pulses;
    receiving Doppler signals and color mode signals representative of receive Doppler pulse signals and receive color mode signals, corresponding to said color pulses and said Doppler pulses; and
    compensating for an effect of said color mode signals on said Doppler signals, including performing one or more filter functions; wherein said performing includes compensating for a weighting of the form sin ($\omega$MT/2), where $\omega$ is the frequency, and M is the interleave factor.

12. A system for ultrasound imaging configured to interleave color mode and Doppler firings, comprising:
    one or more transducers;
    a controller coupled to control interleaved firing of transmit Doppler mode and transmit color mode signals; and
    a Doppler processor operably coupled to said one or more transducers, said Doppler processor configured to compensate for a residue effect received Doppler mode signals, said received Doppler mode signals corresponding to said Doppler mode transmit signals, said residue effect a result of said color mode interleaving.

13. A system according to claim 12, wherein said controller is further configured to control firing of B mode pulses.

14. A system according to claim 13, including a B mode processor operably coupled to said one or more transducers and configured to receive and process B mode signals.

15. A system for ultrasound imaging configured to interleave color mode and Doppler firings, comprising:
   one or more transducers;
   a controller coupled to control interleaved firing of transmit Doppler mode and transmit color mode pulses; and
   a Doppler processor operably coupled to said one or more transducers, said Doppler processor configured to compensate for an effect of said color mode pulses on received Doppler mode signals, said received Doppler mode signals corresponding to said Doppler mode transmit pulses, wherein said Doppler processor is configured to compensate for a weighting factor having the form $\sin(\omega MT/2)$, where $\omega$ is the frequency, and M is the interleave factor.

16. A system according to claim 12, wherein said Doppler processor is configured to execute a weighting correction function at a plurality of frequencies $\omega$ having the form (1/F) where F has the form:

$$F = \begin{cases} \sin\frac{\omega MT}{2}, & \text{if} \left|\sin\frac{\omega MT}{2}\right| \geq \sigma \\ sgn\left(\sin\frac{\omega MT}{2}\right)\sigma, & \text{if} \left|\sin\frac{\omega MT}{2}\right| < \sigma \end{cases}$$

17. A system according to claim 12, wherein said Doppler processor is configured to force predetermined transition Doppler signals to zero and perform one or more filter functions.

18. A system according to claim 12, wherein said Doppler processor is configured to compensate using a window function having a width M.S, where M is an interleave factor and S is a sample size.

19. A system according to claim 12, wherein said Doppler processor is configured to compensate for a weighting of the form $\sin(\omega MT/2)$, where $\omega$ is the frequency and M is the interleave factor.

20. A system according to claim 1, further including:
   means for generating transmit B mode signals; and
   means for receiving receive B mode signals.

21. A system according to claim 1, wherein said compensating means includes means for executing a weighting correction function at a plurality of frequencies $\omega$ having the form (1/F) where F has the form:

$$F = \begin{cases} \sin\frac{\omega MT}{2}, & \text{if} \left|\sin\frac{\omega MT}{2}\right| \geq \sigma \\ sgn\left(\sin\frac{\omega MT}{2}\right)\sigma, & \text{if} \left|\sin\frac{\omega MT}{2}\right| < \sigma \end{cases}$$

22. A system according to claim 1, wherein said compensating means includes means for compensating for a weighting of the form $\sin(\omega MT/2)$, where $\omega$ is the frequency and M is the interleave factor.

* * * * *